(12) United States Patent
Brown et al.

(10) Patent No.: US 7,955,611 B2
(45) Date of Patent: Jun. 7, 2011

(54) BINDING AND RINSE-OFF OF QUATERNARY AMMONIUM COMPOUNDS FOR COSMETIC AND PERSONAL CARE APPLICATIONS

(75) Inventors: James H. Brown, Scottsdale, AZ (US); Keiko Hosohata, Scottsdale, AZ (US); Sambasivarao Koritala, Sun Lakes, AZ (US); David Ashley, Phoenix, AZ (US)

(73) Assignee: International Flora Technologies Ltd., Chandler, AZ (US)

( * ) Notice: Subject to any disclaimer, the term of this patent is extended or adjusted under 35 U.S.C. 154(b) by 138 days.

(21) Appl. No.: 12/203,004

(22) Filed: Sep. 2, 2008

(65) Prior Publication Data
US 2009/0191286 A9 Jul. 30, 2009

Related U.S. Application Data

(63) Continuation-in-part of application No. 10/611,775, filed on Jun. 30, 2003, which is a continuation-in-part of application No. 09/478,071, filed on Jan. 3, 2000, now Pat. No. 7,435,424.

(51) Int. Cl.
*A01N 25/02* (2006.01)
(52) U.S. Cl. ........ 424/405; 424/400; 424/401; 424/406; 424/776; 514/880
(58) Field of Classification Search .................. None
See application file for complete search history.

(56) References Cited

U.S. PATENT DOCUMENTS

| | | | |
|---|---|---|---|
| 2,240,365 A | 4/1941 | Dreger | |
| 2,450,403 A | 9/1948 | Wells | |
| 3,887,537 A | 6/1975 | Harada et al. | |
| 4,172,123 A | 10/1979 | Lowicki | |
| 4,324,802 A | 4/1982 | Koulbanis et al. | |
| 5,159,124 A | 10/1992 | Bertholet | |
| 5,489,431 A | 2/1996 | Ascione et al. | |
| 5,679,393 A | 10/1997 | Laur et al. | |
| 5,705,722 A | 1/1998 | Monnier et al. | |
| 5,759,555 A | 6/1998 | Moy | |
| 5,928,659 A | 7/1999 | Moy | |
| 6,146,616 A | 11/2000 | Msika et al. | |
| 6,280,746 B1 * | 8/2001 | Arquette et al. | 424/401 |
| 6,649,177 B2 * | 11/2003 | Howard et al. | 424/401 |
| 2004/0028641 A1 | 2/2004 | Barone et al. | |

FOREIGN PATENT DOCUMENTS

| | | | |
|---|---|---|---|
| FR | 2471775 | * | 6/1981 |
| GB | 585799 | | 2/1947 |
| GB | 755114 | | 8/1956 |
| GB | 558820 | | 1/1994 |
| JP | 63316714 | | 12/1988 |
| WO | 9421764 | | 9/1994 |
| WO | 9950211 A1 | | 10/1999 |
| WO | 0121605 A2 | | 3/2001 |
| WO | 2001049257 A1 | | 7/2001 |

OTHER PUBLICATIONS

European Patent Office "Office Action" mailed Mar. 15, 2010; European Application No. 04 754 840.9 filed Dec. 29, 2005.
International Searching Authority "International Search Report," for International Application No. PCT/US2004/018354, mailed Dec. 6, 2004.
International Searching Authority "International Search Report," for International Application No. PCT/US2000/035469, mailed Apr. 20, 2001.
Fragrance Journal, Dec. 1993, p. 136-145, vol. 21, issue 12.
Katy Hall, CPI Scientific, "Ultrahydrophytosqualene: New Processes for the Generation of Squalene by Supercritical Fluid Extraction from Waste of Olive Oil Production and Hydrogenation of Squalene," date prepared Feb. 1999; modified Sep. 17, 1999.
Roland Barnaby, Sea Grant News & Notes from Around the Nation, "Roughly Not So Fat After All," Oct. 13, 1995, pp. 1-3; retrieved from the Internet on Dec. 20, 1999 at http://www.seagrantnews.org/news/tips/tips_oct95.htm.
Dr. Peter Nichols, "Marine Oils from Australian Fish: Characterization and Value Added Products," modified Apr. 9, 1998, pp. 1-4; retrieved from the Internet on Dec. 20, 1999 at http://www.frdc.com.au/ub/reports/id/94-115.htm.
M. Bastic et al., "Hydrocarbons and Other Weakly Polar Unsaponifiables in Some Vegetable Oils," Dec. 1978, 2 pages.
V. Paganuzzi, Journal of the American Oil Chemists' Society "On the Composition of Iranian Olive Oil," Dec. 1979, vol. 56, No. 12, 2 pages.
R. J. Maxwell et al., "Determination of the Unsaponifiable Matter in Fatty Acids by a Rapid Column Method," Nov. 1981, pp. 1002-1004.
R. J. Maxwell et al., "Rapid Quantitative Procedure for Measuring the Unsaponifiable Matter from Animal, Marine, and Plant Oils," Jun. 1979, vol. 56, No. 6, pp. 634-636.
R. S. Farag et al., "The Lipids of Various Fungi Grown on an Artificial Medium," Jul. 1981, p. 765.
Daniel P. Schwartz, "Improved Method for Quantitating and Obtaining the Unsaponifiable Matter of Fats and Oils," Feb. 1988, pp. 246-251, vol. 65, No. 2.
M. J. Werman et al., A Simple and Sensitive Method for Detecting Avocado Seed Oil in Various Avocado Oils, 1996, pp. 665-667, vol. 73, No. 5.
O'Connor et al. "Long-Chain Unsaturated Alcohols from Jojoba Oil by Sodium Reduction"; The Journal of the American Oil Chemists' Society, vol. 36, 1958.
Daugherty et al. "Industrial Raw Materials of Plant Origin. IV. A Survey of *Simmondsia chinensis*"; 1956.
European Patent Office "European Search Report," mailed Oct. 27, 2010; Application No. 00 989 549.1-2108.

* cited by examiner

*Primary Examiner* — Neil Levy
(74) *Attorney, Agent, or Firm* — Ingrassia Fisher & Lorenz, P.C.

(57) ABSTRACT

The disclosed composition and method includes the use of non-polar unsaponifiable material and polar hydrophilic salts in conjunction with quaternary ammonium compounds to provide hair treatment preparations for cosmetic and personal care applications. Disclosed features and specifications may be variously controlled, adapted or otherwise optionally modified to improve substantivity and/or rinse-off characteristics. Exemplary embodiments of the present invention generally provide hair conditioners, shampoos, straighteners, permanent waves, color-fast dyes, non-color-fast dyes, and repair treatments with jojoba hydrolysates in combination with Quaternium 80 for increased substantivity and superior wash/rinse-off benefits.

9 Claims, No Drawings

BINDING AND RINSE-OFF OF QUATERNARY AMMONIUM COMPOUNDS FOR COSMETIC AND PERSONAL CARE APPLICATIONS

RELATED APPLICATIONS

This application is a continuation-in-part and claims the benefit of application Ser. No. 10/611,775 filed in the United States Patent and Trademark Office on Jun. 30, 2003 by John C. Hill et al. and is a continuation-in-part of and claims the benefit of application Ser. No. 09/478,071 filed in the United States Patent and Trademark Office on Jan. 3, 2000 by James H. Brown et al.

FIELD OF INVENTION

The present invention relates to novel compositions of matter derived from natural materials and/or extracts of natural materials. In particular the invention relates to substantive carriers derived from natural waxes, oils and other extracts, and in particular, to substantive carriers derived from natural ingredients with relatively high levels of unsaponifiable material. The present invention further describes use of the disclosed novel compounds for improving the binding and rinse-off characteristics of quaternary ammonium compounds in cosmetic and personal care applications.

DETAILED DESCRIPTION

Vegetable and animal fats are composed of organic lipid materials that generally contain esters of long-chain fatty acids and glycerin. Under certain conditions, these esters can react with water to form glycerin and free fatty acids. When heated in the presence of an alkali hydroxide, the esters produce alkali salts of the fatty acid (soaps) and glycerin in a hydrolysis process known as saponification. The terms "saponification" and "saponifying", along with any contextual equivalents thereof are generally used to refer to the hydrolysis reaction between a wax, oil or fat with an alkali metal or alkaline earth metal hydroxide to form the corresponding metallic salt soap. Fats and oils typically have a saponification value that refers to, for example, the number of milligrams of potassium hydroxide required for complete saponification of one gram of free organic acid and/or organic acid ester.

The hydrolyzed products of the saponification process may either be hydrophilic (i.e., water soluble) or hydrophobic (i.e., water insoluble). The term "unsaponifiable" typically refers to hydrolysate products that are generally water insoluble. This is in agreement with A.O.C.S. (American Oil Chemist Society) Official Method Ca 6b-53, which defines unsaponifiable materials as substances generally found as components of fats and oils which cannot be saponified by ordinary caustic treatments, but which are soluble in ordinary fats and oils. Unsaponafiable components may include, but are not limited to, higher aliphatic alcohols, sterols, pigments, mineral oils, tocopherols, hydrocarbons and the like. Unsaponifiable materials are generally non-volatile at 103° C. and the weight percent (wt. %) of unsaponifiable material in a substance may be characterized by measuring the weight percent of those materials defined as unsaponifiable.

Most well-known vegetable and animal lipids generally have low levels (i.e., less than five percent [5%]) of unsaponifiable materials. Accordingly, the majority of the hydrolysate products of the saponification reaction of these lipids are water-soluble. Conventional vegetable oils typically have levels of unsaponifiable material generally below 1%. For example, saponification of soybean oil leaves about 0.7 wt. % unsaponifiable materials, saponification of olive oil leaves about 1.2 wt. % unsaponifiable materials, and saponification of peanut oil leaves about 0.4 wt. % unsaponifiable materials. However, some commercial oils are known to contain higher concentrations of unsaponifiable components; for example, up to as much as 6.0 wt. % unsaponifiable material. Representative examples include: crude rice bran oil (about 4.2 wt. % unsaponifiable), crude wheat germ oil (about 6 wt. % unsaponifiable), and shea butter (9-13 wt. % unsaponifiable). Materials with high levels of unsaponifiables (e.g., shea butter) are generally not a preferred starting material for conventional soap production due to the relatively high amount of unsaponifiable materials left after saponification.

In most cases, the hydrolysates of a saponification process are generally used as hygienic skin-cleansing agents (soaps). In the past, animal fat (lard or tallow) was mixed with wood ash (lye) to produce soap. Preferably, a bar of soap has a suitable hardness to maximize cycles of use and resistance to water re-absorption when not in use, while at the same time providing sufficient lather to enhance the cleansing ability of the soap. Saponified animal lipids will generally meet these user demands to some extent. Modern soap production continues to rely heavily on animal fats in their composition to meet consumer demand and production requirements, although more and different types of synthetic materials are beginning to find use in conventional soaps. A variety of synthetic compounds have become popular ingredients in modern soap-making processes due, in part, to the improvements they impart to soap quality and user satisfaction; however, synthetic-based soaps are generally not biodegradable and thus persist to some extent in the environment.

There are generally two types of soap manufacturing processes. In a first method, oils and fats are boiled in an open kettle with caustic alkali solution(s), bringing about saponification gradually until substantially all of the fats and oils are saponified, followed by the removal of glycerin that is produced as a byproduct. This process may either run in a batch mode or in a continuous process. In a second method, which is generally a continuous method (but may also be performed in a batch mode), fatty acids and alkali components are brought together in proper portions for substantially complete saponification in a mixing valve or other containment device. The progress of the saponification reaction generally depends on temperature, time of contact, and efficiency of mixing. Concentrated solutions produced by these methods are referred to as "neat" soaps and typically possess a concentration of 60-65% soap, about 35% water, as well as trace amounts of salt and glycerin. It is from these types of products that consumer soaps in the form of bars, flakes, granules and powders are produced—for example, by first drying the neat soap into pellets having a moisture content of about 12-16 wt. % followed by finishing steps, such as milling, plodding, amalgamating, and/or the like.

Many conventional bar soaps are manufactured from coconut oil and/or tallow, or their corresponding fatty acids. Palm kernel oil is sometimes substituted for coconut oil for economic reasons, and soaps prepared with palm kernel oil are typically adjusted to provide performance characteristics similar to non-substituted tallow/coconut formulations. Palm oil is also often substituted for tallow in a variety of other applications.

One consideration in selecting materials for making soap is a proper ratio of saturated versus unsaturated, and long-versus-short-chain fatty acids that result in a soap having the desired qualities of stability, solubility, ease of lathering, hardness, cleaning ability, and/or the like.

It has been demonstrated that soaps prepared from mixtures where a majority of the fatty acids have carbon chain-lengths less than twelve atoms generally irritate the skin. Soaps prepared from saturated C16 and C18 fatty acids are typically too insoluble for consumer use. Accordingly, conventionally preferred materials for soap production generally have fatty acid chain-lengths between twelve and eighteen carbon atoms in length.

Saponification of tallow typically produces soaps having a mixture of fatty acids corresponding to C14:0, C16:0, C18:0 and C18:1 (myristic, palmitic, stearic and oleic acids, respectively), while saponification of coconut oil typically produces soaps having a mixture of fatty acids of C12:0 and C14:0 (lauric acid and myristic acid, respectively) as well as significant amounts of C8:0 and C10:0 fatty acids. Conventional consumer soaps typically have tallow/coconut (T/C) ratios ranging from approximately 90:10 to 75:25. Since lauric acid is found only in the coconut fraction, the most dramatic change observed in increasing the percent of the coconut fraction of T/C mixtures is the increase in the lauric acid. Increasing the coconut fraction in T/C soaps generally improves desirable foaming characteristics; however, in soaps with T/C ratios of 50:50, the desirable skin mildness properties are somewhat reduced.

Typical fatty acid distributions (in wt. %) for conventional soap making components include:

| Carbon Chain-Length | Tallow | Palm | Coconut | Palm Kernel |
|---|---|---|---|---|
| 10:0 (capric) | 0.1 | 0.0 | 15.1 | 6.4 |
| 12:0 (lauric) | 0.1 | 0.3 | 48.0 | 46.7 |
| 14:0 (myristic) | 2.8 | 1.3 | 17.5 | 16.2 |
| 16:0 (palmitic) | 24.9 | 47.0 | 9.0 | 8.6 |
| 18:0 (stearic) | 20.4 | 4.5 | 9.0 | 8.6 |
| 18:1 (oleic) | 43.6 | 36.1 | 5.7 | 16.1 |
| 18:2 (linoleic) | 4.7 | 9.9 | 2.6 | 2.9 |
| 18:3 (linolenic) | 1.4 | 0.2 | 0.0 | 0.0 |
| 20:0 (arachidic) | 1.8 | 0.3 | 0.0 | 0.4 |

From this data, it can be seen that coconut and palm kernel fats (both known as "lauric fats") are particularly rich in the C10-C14 saturated fatty acids. Another fat that contains saturated, relatively short-chain fatty acids similar to coconut oil is babassu oil. In contrast, tallow and palm oil are per se industrial sources of non-lauric fats, especially those containing C16 and C18 fatty acids.

In general, the longer chain fatty acid alkali salts, particularly the less expensive C16 and C18 salts (as obtained from tallow and palm oils), generally provide structure in finished soap bars and also operate to prevent, or otherwise retard, disintegration of the soap bar on exposure to water. The more expensive, shorter chain, lauric fat-derived, (i.e., lauric acid salts) and other soluble salts (typically as obtained from coconut and palm kernel oil) contribute to the lathering properties of the overall composition. A general problem in the formulation of bar soaps has been finding a balance between providing structure (generally obtained from the long chain components) and maintaining lathering properties (generally obtained from the more expensive short chain components) at a practical overall cost.

In addition to fatty acid salts, conventional soap bars may also be adapted to contain excess (free) fatty acids. The addition of free fatty acids is known as superfatting, which at a level of 5-10% generally imparts a copious, creamy lather to the soap. Other superfatting agents that may be used include citric and other acids that function by promoting the formation of free fatty acids in the soap blend.

The pharmaceutical and cosmetic industries have been using lipid extracts of vegetable origin since earliest times. A number of years ago it became apparent in these industries that particularly valuable biological benefits resulted from the use of vegetable fats or extracts of vegetable fats rich in unsaponifiable materials. Certain vegetable oils (e.g., avocado and shea) are known to be particularly rich in unsaponifiable materials.

A process for enriching unsaponifiable compounds in oils (such as shea butter, for example) for use in cosmetic and pharmaceutical compositions is described in U.S. Pat. No. 5,679,393 to Laur. This process concentrates the unsaponifiable fraction of fats and oils by a process of crystallization and fractionation. This method is expensive and does not liberate the alcohol moiety from the starting compounds. Accordingly, the Laur process does not disclose the utilization of hydrolysis to create alkali salts with the liberation of alcohols and other unsaponifiables.

Hydrolysates applied topically to animate and inanimate objects find use in numerous non-cleansing applications including cosmetic preparations, pharmaceuticals, hydration formulations, insecticides, insect repellant, and the like. One of the areas of interest is in the maximization of the duration a topically applied active agent resides on the applied surface (substantivity). The search for ways to improve the duration that a topically applied cosmetic, pharmaceutical and/or bioactive agent resides on its surface of application has been of importance in several areas where topically applied cosmetics, pharmaceuticals and/or bioactive agents are employed. An example of this interest may be found in the conventional art relating to sunscreen formulations.

Prior to Applicants' previous work, conventional cosmetics and other applications have not utilized hydrolysates of naturally derived materials containing high unsaponifiables of long chain esters (i.e., greater than 18 carbons in length) to enhance the substantivity of topically applied agents with which they are incorporated. Previously, the purpose of employing polymers or other synthetic materials in conventional compositions has been directed towards improving adherence of these materials to the skin or as thickening agents. The improved substantivity, among other beneficial properties, achieved by employing hydrolysates in accordance with the present invention has not heretofore been disclosed or otherwise appreciated in the conventional art.

The increased substantivity of topically applied agents provides for more effective and economical use of these materials. In particular, the present invention provides improved compositions for boosting the binding (substantive) properties and the rinse-off characteristics of quaternary ammonium compounds in cosmetic and personal care applications.

Quaternary ammonium cations, also known as "quats", are positively charged polyatomic ions of the structure $NR_4^+$ with R corresponding to alkyl groups. Unlike the ammonium ion $NH_4^+$ itself (and primary, secondary, or tertiary ammonium cations), quaternary ammonium cations are permanently charged, independent of the pH of their solution. Quaternary ammonium cations may be synthesized by alkylation of ammonia or other amines.

Quaternary ammonium salts or quaternary ammonium compounds are salts of quaternary ammonium cations with an anion. They are principally used as disinfectants, surfactants, fabric softeners and as antistatic agents (e.g., in shampoo). In liquid fabric softeners, the chloride salts are often used. In dryer anti-cling pads, the sulfate salts are often used, They are also common ingredients in many spermicidal jellies.

The need for conditioning the hair after washing is to some extent due to the exceptional cleaning performance of modern shampoos. Frequent shampooing and fashion treatments (e.g., waves, dyes, straighteners and the like) leave hair lacking in luster, difficult to comb, damaged and prone to fly-away. These problems may be mitigated with proper selection and use of conditioning agents in shampoos, or through a variety of treatments such as with cream rinse, pomade, hot oil or intensive conditioner. Modern consumers demand a wide variety of choices targeted to specific hair types and user needs.

Cosmetic formulators must meet the demands for economy and performance required by an increasingly specialized market. Never before has such a variety of conditioning materials been at the disposal of cosmetic chemists. That notwithstanding, most contemporary conditioner actives continue to feature quaternary ammonium salts as prominent ingredients on the labels of many popular brands.

The chemical structure of quaternary ammonium salts makes them substantive to hair and ideally suited for conditioning applications. Quats also enjoy an unrivalled popularity in the cosmetic and detergent industries and pound for pound, are one of the most cost-effective conditioning agents in use today. They are quite versatile and few other chemicals can rival them for their structural and functional qualities, which enable chemists to tailor formulas around specific requirements. By understanding the functional characteristics of quaternary ammonium salts, the cosmetic chemist can select the product or combination of products which provide the solubility, substantivity and conditioning features most appropriate for the targeted consumer.

Knowledge of solubility is generally beneficial to guide the formulator in selecting a quaternary ammonium compound which will be compatible with the system under development. For example, clear conditioners must be developed from water-or glycol-soluble quaternaries, while opaque systems permit the formulator enough latitude to choose soluble, dispersible, emulsifiable or even pearlescent materials.

Long chain di-alkyl and tri-alkyl chloride quats generally display a tendency to build up or "over-condition" hair if applied in excess or chronically. By formulating products such as tricetylmonium chloride at low concentrations, these quats can function as auxiliary agents in light-or medium-conditioning formulas.

Not surprisingly, longer chain quaternaries have achieved their greatest popularity in the intensive conditioner market. Intensive conditioners are used one to three times weekly to supplement daily shampoo/cream rinse regimens. They are also recommended for hard-to-manage and damaged hair.

PEG-2 oleamonium chloride was found to be an effective antistatic agent for normal and waved hair, both in laboratory tests and practical application. This suggests applications for ethoxylates in light, frequent-use conditioner regimens. Such products may also be targeted to people with fine hair.

The performance of mono-alkyl quaternary salts also varies as a function of chain length. Mono-alkyl quats are relatively easy to formulate and generally provide light to moderate conditioning. Long chain mono-alkyl or di-alkyl quats provide superior ease of wet or dry combing. Long chain di-alkyl quaternaries offer excellent static control and are the generally preferred choice for use with difficult-to-manage or damaged hair. The intensive conditioning profile and good substantivity of di-alkyl quats also suggest uses as a treatment for bleached, waved or dyed hair.

The following representative descriptions of the present invention generally relate to exemplary embodiments and the inventors' conception of the best mode, and are not intended to limit the applicability or configuration of the invention in any way. Rather, the following description is intended to provide convenient illustrations for implementing various embodiments of the invention. As will become apparent, changes may be made in the function and/or arrangement of any of the elements described in the disclosed exemplary embodiments without departing from the spirit and scope of the invention.

Various representative implementations of the present invention may be applied to any system for providing treatments to the hair of an animal subject. Certain representative implementations may include, for example: improved binding of a conditioning agent to the hair; improved rinse-off of a conditioning agent from the hair; improved binding of a coloring agent to the hair; improved rinse-off of a coloring agent from the hair; improved binding of a repairing agent to the hair; improved rinse-off of a repairing agent from the hair; improved binding of a curling agent to the hair; improved rinse-off of a curling agent from the hair; improved binding of a straightening agent to the hair; improved rinse-off of a straightening agent from the hair; and/or the like.

The present invention is a formulation composition, and method for using the same, which is useful to improve the substantivity and rinse-off characteristics of quaternary ammonium compounds. Additionally, the composition is useful for carrying an effective amount of topically applied active materials. More specifically, compositions in accordance with representative aspects of the present invention generally provide a vehicle for the topical application of materials to the hair of an animal subject when superior "lasting" power or substantivity is required. Additionally, the present invention is useful because, among other things, it acts as both an emollient and unique emulsifier while demonstrating substantivity and has the ability to "fix" many different types of "active" materials.

"High unsaponifiable materials" or "high unsaponifiable content" oils, waxes, fats, and the like shall be understood to correspond to compositions that comprises at least 5% by weight of total organic materials that are unsaponifiable and at least 10% (but up to in excess of 95%) by weight of organic materials that are saponifiable. Accordingly, the term "high unsaponifiable" shall be deemed to reference compositions containing from 5-90% by weight of organic unsaponifiable materials and 10-95% by weight of saponifiable materials. Examples of bio-based materials with high unsaponifiables may be found in Applicants' co-pending U.S. patent application Ser. No. 09/478,071 (now U.S. Pat. No. 7,435,424).

"Substantivity" generally refers to the tendency of a material to resist being easily removed or the persistence of a treatment to remain on the skin or hair. For example, some sunscreen lotions are substantive because they form a film on the skin that is relatively water-insoluble. Accordingly, substantive materials resist removal or transfer by physical contact, sweating or washing.

Compositions of matter comprising waxes, oils and/or fats (lipids) containing at least 5% by weight unsaponifiable ingredients and at least 10% by weight saponifiable ingredients are subjected to an alkaline hydrolysis reaction to produce a non-foaming, substantive composition with unique surfactant properties that may be used as an active ingredient or as a carrier for application of other active ingredients—e.g., as a vehicle for application of cosmetic, pharmaceutical or other active ingredients to the hair of an animal subject. Commercially available bio-based extracts that have high unsaponifiables include, but are not limited to, candelilla wax, carnauba wax, jojoba oil, lanolin, lecithin, Shea butter and/or the like.

The extracts used as starting materials for the hydrolysis reaction according to the method of the present invention may be in their raw or refined states. The extracts may also be alkoxylated, polymerized, acetylated, oxidized, reduced, concentrated, hydrogenated, partially hydrogenated, interesterified, double bond modified, randomized, refined, or otherwise modified before the hydrolysis reaction. Since many lipids have low concentrations or fractions (for example 1% or less) of unsaponifiables, the present invention encompasses the concentration of low fraction unsaponifiables into higher fractions—i.e., greater than 5%.

The products from the hydrolysis reaction of organic materials that produce unsaponifiables comprise a mixture of: (a) polar hydrophilic salts (saponifiables); and (b) non-polar, lipophilic materials (unsaponifiables), with the possibility of other materials also present, depending on the source, state and form of the initial reactant.

The composition of materials created by the method according to the present invention are produced by the reaction of aqueous alkali metal hydroxides and earth hydroxides—e.g., NaOH, LiOH, KOH, CaOH, MgOH, and/or the like, with organic lipid compositions, usually plant extracts, oils, fats, or waxes (or the extracts or derivatives of the extracts) where the organic compositions contain a relatively high proportion of unsaponifiable materials (greater than 5%), and preferably as long-chain esters.

Jojoba oil may be examined as a representative case. Refined jojoba oil contains various proportions of long-chain di-unsaturated esters. Hydrolysates of refined jojoba oil are nearly a 55:45 mixture of polar hydrophilic long chain salts (alkali salts) and relatively non-polar lipophilic materials (fatty alcohols).

One of the above-mentioned properties, substantivity, is particularly useful in the field of shampoos, conditioners, hair sheens, hair dyes, and hair relaxers. The property of substantivity is especially beneficial to hair care products, such as "leave in" hair conditioners, where naturally derivatized materials that display substantivity are particularly commercially desirable.

The composition according to the present invention is preferably produced in a batch process using a large steam kettle equipped with a propeller mixer. A measured quantity of potassium hydroxide pellets are added into the steam kettle with a measured quantity of distilled, deionized, or reverse osmosis purified water. The amount of potassium hydroxide employed in order to completely saponify the free organic acid and/or organic acid ester may be calculated from the Saponification Value of the starting material and will, in theory, correspond to a stoichiometric amount. In practice, however, it may be preferred to employ slightly less than the stoichiometric amount of potassium hydroxide in order to ensure that the hydrolysates that are formed are not contaminated with unused alkali. The amount of potassium hydroxide employed may be considerably less than the stoichiometric amount, for example, as little as 50% of the stoichiometric amount or less may be employed depending upon the desired result. It should be understood, however, that an amount of potassium hydroxide in excess of the stoichiometric amount (e.g., up to 10% more than the stoichiometric amount) may be employed if complete saponification of the organic acid or ester is to be achieved. Excess potassium hydroxide remaining at the end of the reaction may be removed by conventionally known methods.

The potassium hydroxide pellets and water are stirred together with the propeller mixer until the potassium hydroxide pellets are substantially dissolved. It is important to note, for safety purposes, that heat is generated during this step and the mixture is quite caustic. Individuals nearby should wear gloves, eye and face protection, and clothing protection to avoid thermal and/or chemical burns.

Next, a measured quantity of a refined or derivatized organic material containing a high proportion of unsaponifiables, such as jojoba oil, is gently added to the steam kettle, taking care not to splash the caustic solution contained therein.

The steam kettle is heated to 90-95° C. and held at that temperature range under constant agitation for two hours. At this point, the resultant mixture should be pH tested. If the solution pH is greater than 10.0, continue heating the mixture under constant agitation at 90-95° C. Retest the solution periodically until the pH is 10.0 or less.

Once the pH is 10.0 or less, withdraw a sample for analysis. This sample should be analyzed by such methods as gas or liquid chromatography or by another similar method, to show that the reaction has proceeded as desired.

The resultant hydrolysate may then be diluted by adding a second measured quantity of water, or other diluent, to the steam kettle and stirred with the mixing propeller. Heat should be continuously applied (less than 80° C.) until the mixture is substantially homogeneous. Once homogeneous, the hydrolysate mixture is cooled to 60° C. while continuing the mixing with the propeller. The hydrolysate mixture may then be transferred to a holding container and allowed to cool to room temperature before sealing the holding container.

Rubine Dye is an anionic dye which will readily react with cationic quats. When light blonde hair or wool is treated with a cationic hair treatment and rinsed, the hair or wool turns reddish pink when dipped into a dilute solution of Rubine Dye. The control (no cationic quat) will remain undyed. For a detailed explanation of the Rubine Dye test procedure, see U.S. Pat. No. 3,769,398.

The following seven (7) samples were processed using the Rubine Dye procedure:

| SAMPLE | K-20W (g) | Q-80 (g) | Water (g) | TOTAL (g) |
|---|---|---|---|---|
| A | 0.10 | 0.40 | 49.50 | 50 |
| B | 0.15 | 0.25 | 49.60 | 50 |
| C | 0.30 | 0.30 | 49.40 | 50 |
| D | 0.40 | 0.35 | 49.25 | 50 |
| E | 0.37 | 0.10 | 49.53 | 50 |
| F | 0.12 | 0.00 | 49.88 | 50 |
| G | 0.00 | 0.15 | 49.85 | 50 |

K-20W corresponds to a mixture of water (80 wt. % of K-20W) and the products resulting from the saponification of jojoba oil, which products (20 wt. % of K-20W) constitute a mixture of 10%-55% (wt./wt.) non-polar unsaponifiables and 45%-90% (wt./wt.) polar hydrophilic salt fraction, where the non-polar unsaponifiable fraction and the polar hydrophilic salt fraction total 100% of the jojoba-derived material, and where the jojoba-derived material corresponds to the tandem in situ reaction products of saponification of jojoba oil starting material having about 45% unsaponifiable material (wt./wt. of jojoba oil) prior to saponification. K-20W is available from International Flora Technologies, Ltd., Chandler, Arizona, USA.

Q-80 corresponds to Quaternium-80 (ABIL QUAT 3272, available from Evonik Goldschmidt Corp., Hopwell, Va., USA).

Sample A corresponded to 0.10 grams of K-20W in combination with 0.40 grams of Q-80 diluted with 49.50 grams of water.

Sample B corresponded to 0.15 grams of K-20W in combination with 0.25 grams of Q-80 diluted with 49.60 grams of water.

Sample C corresponded to 0.30 grams of K-20W in combination with 0.30 grams of Q-80 diluted with 49.40 grams of water.

Sample D corresponded to 0.40 grams of K-20W in combination with 0.35 grams of Q-80 diluted with 49.25 grams of water.

Sample E corresponded to 0.37 grams of K-20W in combination with 0.10 grams of Q-80 diluted with 49.53 grams of water.

Sample F corresponded to 0.12 grams of K-20W diluted with 49.88 grams of water.

Sample G corresponded to 0.15 grams of Q-80 diluted with 49.85 grams of water.

Samples A thru G were applied to individual fresh wool swatches (one for each sample) which were then subject to Rubine Dye testing to determine the adherency (i.e., substantivity) of the Q-80 to the wool fiber. The swatches were lined up in a uniformly illuminated field in a single photographic exposure. ADOBE PHOTOSHOP (Adobe Systems, Inc. San Jose, Calif., USA) was used to determine localized color saturation for each of the swatch areas in the photographic field. The photographic exposure was subjected to a Gaussian blur with a radius of ten (10) pixels to account for small-scale fluctuations in color saturation. The following saturation values were measured:

| SAMPLE | RELATIVE SATURATION (%) |
|---|---|
| A | 86 |
| B | 91 |
| C | 97 |
| D | 98 |
| E | 84 |
| F | 16 |
| G | 69 |

The saturation data clearly demonstrates improved binding (i.e., substantivity) of Q-80 in the presence of K-20W in accordance with various representative aspects of the present invention. Additionally, in trials where the wool swatches were washed after application of the sample K-20W/Q-80 solutions, but before performing the Rubine Dye assay, it was observed that increasing the K-20W component relative to the reminder of the formulation operated to provide improvement of the wash-/rinse-off characteristics resulting in easier liberation of the Q-80 from the wool swatches. This particular aspect of Applicants' invention provides substantial benefits for the removal of quat build-up on the hair of a subject upon repeated use.

In the foregoing specification, the invention has been described with reference to specific exemplary embodiments; however, it will be appreciated that various modifications and changes may be made without departing from the scope of the present invention as set forth in the claims below. The specification and figures are to be regarded in an illustrative manner, rather than a restrictive one and all such modifications are intended to be included within the scope of the present invention. Accordingly, the scope of the invention should be determined by the claims appended hereto and their legal equivalents rather than by merely the examples described above.

For example, the steps recited in any method or process claims may be executed in any order and are not limited to the specific order presented in the claims. Additionally, the components and/or elements recited in any apparatus claims may be assembled or otherwise operationally configured in a variety of permutations to produce substantially the same result as the present invention and are accordingly not limited to the specific configuration recited in the claims.

Benefits, other advantages and solutions to problems have been described above with regard to particular embodiments; however, any benefit, advantage, solution to problem or any element that may cause any particular benefit advantage or solution to occur or to become more pronounced are not to be construed as critical, required or essential features or components of any or all the claims.

As used herein, the terms "comprising", "having", "including" or any contextual variant thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

We claim:

1. A hair treatment composition for application to the hair of an animal subject, said composition comprising:
   jojoba-derived material comprising a 10%-55% (wt./wt.) non-polar unsaponifiable fraction and a 45%-90% (wt./wt.) polar hydrophilic salt fraction, wherein said non-polar unsaponifiable fraction and said polar hydrophilic salt fraction total 100% of said jojoba-derived material, and wherein said jojoba-derived material corresponds to the tandem reaction products of saponification of jojoba oil starting material having about 45% unsaponifiable material (wt./wt. of jojoba oil) prior to saponification; and
   a quaternary ammonium compound.

2. The composition of claim 1, wherein said jojoba oil starting material is pre-treated prior to saponification and the method of pre-treatment comprises at least one of:
   alkoxylation, polymerization, acetylation, oxidation, reduction, concentration, hydrogenation, partial hydrogenation, interesterification, double bond modification, randomization and refinement.

3. The composition of claim 1, wherein said quaternary ammonium compound comprises Quaternium-80.

4. A method for improving the substantive characteristics of a hair treatment preparation, said method comprising the step of administering a composition to the hair of an animal subject, said composition comprising:
   jojoba-derived material comprising a 10%-55% (wt./wt.) non-polar unsaponifiable fraction and a 45%-90% (wt./wt.) polar hydrophilic salt fraction, wherein said non-polar unsaponifiable fraction and said polar hydrophilic salt fraction total 100% of said jojoba-derived material, and wherein said jojoba-derived material corresponds to the tandem reaction products of saponification of jojoba oil starting material having about 45% unsaponifiable material (wt./wt. of jojoba oil) prior to saponification; and a quaternary ammonium compound.

5. The method of claim 4, wherein said jojoba oil starting material is pre-treated prior to saponification and the method of pre-treatment comprises at least one of:

alkoxylation, polymerization, acetylation, oxidation, reduction, concentration, hydrogenation, partial hydrogenation, interesterification, double bond modification, randomization and refinement.

6. The method of claim 4, wherein said quaternary ammonium compound comprises Quaternium-80.

7. A method for improving the rinse-off characteristics of a hair treatment preparation, said method comprising the step of administering a composition to the hair of an animal subject, said composition comprising:

jojoba-derived material comprising a 10%-55% (wt./wt.) non-polar unsaponifiable fraction and a 45%-90% (wt./wt.) polar hydrophilic salt fraction, wherein said non-polar unsaponifiable fraction and said polar hydrophilic salt fraction total 100% of said jojoba-derived material, and wherein said jojoba-derived material corresponds to the tandem reaction products of saponification of jojoba oil starting material having about 45% unsaponifiable material (wt./wt. of jojoba oil) prior to saponification; and a quaternary ammonium compound.

8. The method of claim 7, wherein said jojoba oil starting material is pre-treated prior to saponification and the method of pre-treatment comprises at least one of:

alkoxylation, polymerization, acetylation, oxidation, reduction, concentration, hydrogenation, partial hydrogenation, interesterification, double bond modification, randomization and refinement.

9. The method of claim 7, wherein said quaternary ammonium compound comprises Quaternium-80.

* * * * *